US00PP10870P

United States Patent [19]

Bull

[11] Patent Number: Plant 10,870

[45] Date of Patent: Apr. 27, 1999

[54] NEW GUINEA IMPATIENS PLANT NAMED 'NATHALIE'

[76] Inventor: Norbert Bull, Gaertnersiedlung 2, Goennebek, Germany

[21] Appl. No.: 08/897,983

[22] Filed: Jun. 23, 1997

[30] Foreign Application Priority Data

Nov. 20, 1996 [DE] Germany ..... IM 417

[51] Int. Cl.[6] ..... A01H 5/00

[52] U.S. Cl. ..... Plt./318

[58] Field of Search ..... Plt./87.6, 318

[56] References Cited

U.S. PATENT DOCUMENTS

P.P. 8,360 8/1993 Bull ..... Plt./87.6

OTHER PUBLICATIONS

GTITM UPOVROM Citation for 'Nathalie' As Per De PBR IM 00417, Jan. 15, 1997.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Nathalie', characterized by its bright orange-red flower color, large flowers borne well above the foliage, very dark green, almost blackish foliage, medium plant habit, and early to medium flowering response.

1 Drawing Sheet

The present invention comprises a new and distinct cultivar of New Guinea Impatiens, referred to by the cultivar name 'Nathalie'.

'Nathalie' is a product of a planned breeding program and was originated from a hybridization made by the inventor Norbert Bull in a controlled breeding program in Goennebek, Germany, in 1993. The female parent was a seedling designated No. 6 and the male parent was a seedling designated No. 10. Both parents are proprietary cultivars used in the breeding program.

'Nathalie' was discovered and selected as one flowering plant within the progeny of the stated cross by the inventor in 1994 in a controlled environment in Goennebek, Germany.

The first act of vegetative or asexual reproduction of 'Nathalie' was accomplished when cuttings were taken from the initial selection in Autumn 1994 in a controlled environment in Goennebek by, or under the supervision of, Norbert Bull.

Horticultural examination of plants grown from these cuttings initiated in Spring 1995 in Goennebek, Germany, and continuing thereafter, has demonstrated that the combination of characteristics as herein disclosed for 'Nathalie' are firmly fixed and are retained through successive generations of asexual reproduction.

'Nathalie' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Nathalie', which in combination distinguish this impatiens as a new and distinct cultivar:

1. Bright orange-red flower color.
2. Large flowers, borne well above the foliage.
3. Very dark green, almost blackish foliage.
4. Medium plant habit.
5. Early to medium flower response.

6. Resistant to powdery mildew.

Of the many commercial cultivars known to the present inventor, the most similar in comparison to 'Nathalie' is the cultivar 'Marpesia' disclosed in U.S. Plant Pat. No. 8,401.

In comparison to 'Marpesia', 'Nathalie' has lighter orange colored flowers (R.H.S. 40 A compared to 43 A for 'Marpesia'), narrower flower shape, more ovate shaped and even darker colored leaves, and a more compact plant habit.

The accompanying colored photographic drawing shows typical flower and foliage characteristics of 'Nathalie', with colors being as true as possible with illustrations of this type. In this regard, the colors in the illustration appear lighter than the actual R.H.S. values for 'Nathalie'. The lighting is bright as to give the appearance of lighter, less-intense hues. The illustration depicts a relatively immature cultivar.

In the following description color references are made to The Royal Horticultural Society Colour Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and then grown in a greenhouse at 20° C. minimum temperature.

Classification:

*Botanical.*—A hybrid of the genus Impatiens.

*Commercial.*—New Guinea Impatiens cv 'Nathalie'.

Plant

A. General appearance and form:

*Height.*—10 cm (10 week old plants).

*Width.*—26 cm.

*Internode length.*—10–20 mm (short).

*Stem color.*—Mainly dark red, greenish stripes.

*Lasting quality of the bloom.*—Approximately two to three weeks.

*Flowerinq response.*—About 8 weeks after planting of rooted cuttings.

*Rooting.*—Color is R.H.S. 159 B-C; roots initiate in about 18 days at 22° C., from sticking to transplanting; no distinguishing rooting habit.

*Flowering season.*—Generally indeterminate, mainly from March to October, depending on light intensity.

*Plant growth.*—Indeterminate, although weak after flowering begins.

B. Foliage:

*Leaf arrangement.*—Primarily in whorls, with the aspect of the leaves almost horizontal.

*Shape of leaf.*—Ovate, with rounded or acute base, and a lightly acumilate tip.

*Margin.*—Slightly serrated, ciliated.

*Leaf, length.*—About 130 mm.

*Leaf, width.*—About 40–47 mm.

*Main color of upper surface.*—Greenish black, slightly olive marbled, mainly R.H.S. 139 A.

*Veins on upper surface, color.*—Light red.

*Variegation on leaf.*—Absent.

*Main color of lower surface.*—Dark red, about R.H.S. 185 A.

*Veins on lower surface, color.*—Dark red.

*Petiole, color.*—Medium to dark red.

*Petiole, length.*—About 10 mm.

Inflorescence

A. Flower:

*Flower number per node.*—About 5–7, in various stages of development, usually one flower per leaf; flowers are borne well above the surface of the leaf canopy.

*Form of corolla.*—Single, somewhat zygomorph, upper petal cupped.

*Average length.*—6.8 cm.

*Average width.*—5.6 cm.

*Color (general tonality from a distance of three meters)*.—Orange-red.

*Petal number.*—Five (5).

*Petal shape.*—Heart-shaped, moderately lobed.

*Petal size.*—Lower and upper petals are about 32–35 mm in width and 28–32 mm in length, and side petals are about 25 mm in width and about 28 mm in length.

*Petal texture.*—Smooth, slightly glossy.

*Main color of upper surface.*—R.H.S. 40 A.

*Color of lower surface.*—R.H.S. 41 B.

*Eye zone.*—Hardly visible, pink, R.H.S. 57 D.

*Spur, color.*—R.H.S. 53 D.

*Spur shape and size.*—Downwardly curved, about 50 mm in length.

*Pedicel, color.*—Light green.

B. Reproductive organs:

*Androecium.*—Stamens: Five (5) in number, fused, upper surface color is mainly R.H.S. 44 A. Anthers: Hooded, color is about R.H.S. 11 D. Pollen: Color is about R.H.S. 4 D.

*Gynoecium.*—Stigma and style: Five (5) in number, very short, color is about R.H.S. 60 A. Ovary: Five (5) celled, 3–5 mm in length, surface color is R.H.S. 139 A.

I claim:

1. A new and distinct cultivar of New Guinea Impatiens plant named 'Nathalie', as illustrated and described.

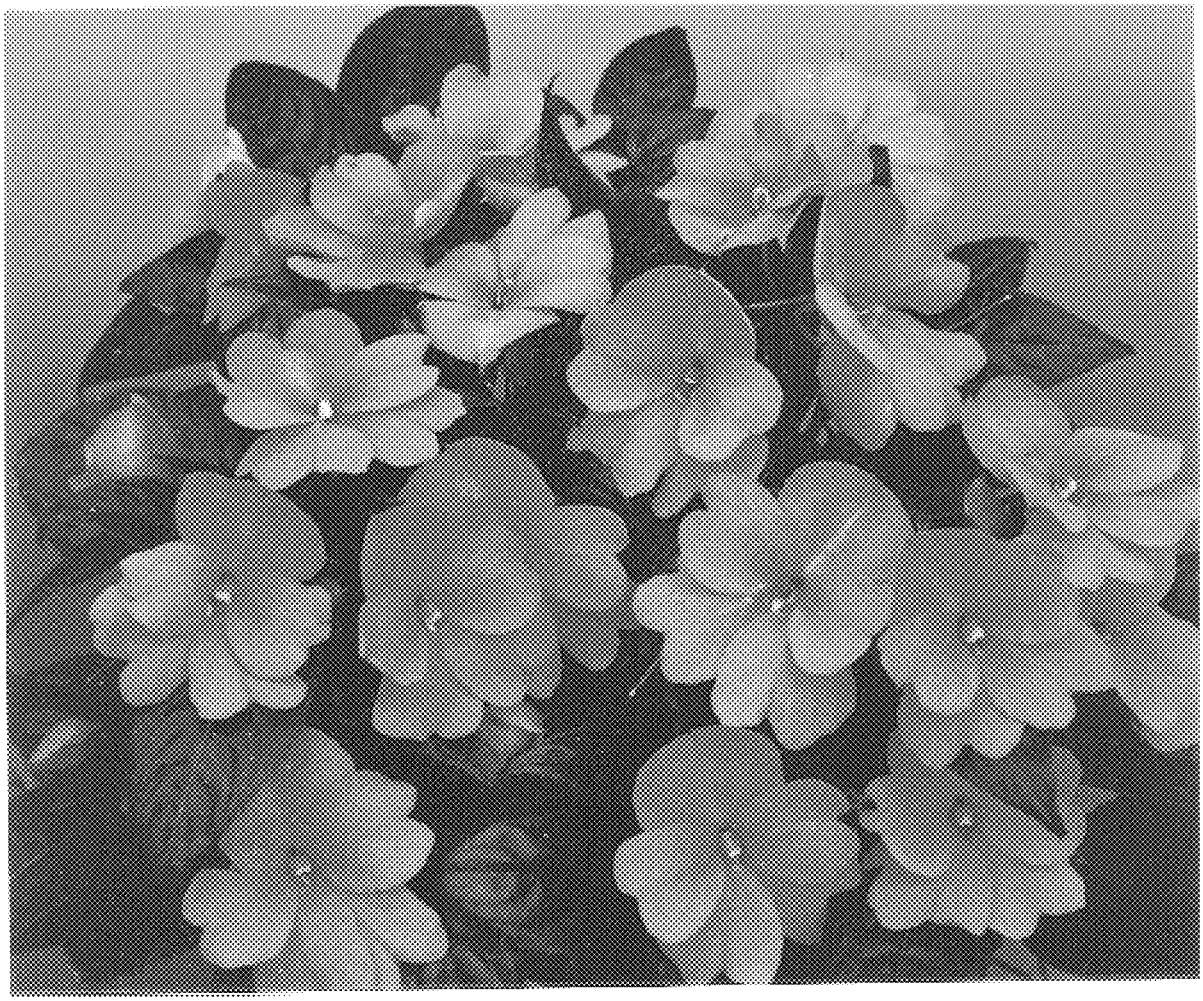

* * * * *